United States Patent [19]

Okabe et al.

[11] Patent Number: 5,611,339
[45] Date of Patent: Mar. 18, 1997

[54] PRINTED ELECTRODE FOR BIOLOGICAL USE

[75] Inventors: Keiichiro Okabe; Toyoji Hibi, both of Tokyo, Japan

[73] Assignees: Kabushiki Kaisya Advance, Tokyo; Hisamitsu Pharmaceutical Co., Inc., Tosu, both of Japan

[21] Appl. No.: 389,333

[22] Filed: Feb. 14, 1995

[30] Foreign Application Priority Data

Feb. 16, 1994 [JP] Japan ................................ 6-040580

[51] Int. Cl.$^6$ ................................................ G01N 27/30
[52] U.S. Cl. ........................................ 128/639; 128/640
[58] Field of Search ................................. 128/639–644

[56] References Cited

U.S. PATENT DOCUMENTS

| | | | |
|---|---|---|---|
| 4,995,960 | 2/1991 | Wiles et al. | 204/418 |
| 5,356,625 | 10/1994 | Ying | 424/94.1 |
| 5,445,829 | 8/1995 | Paradissis et al. | 424/480 |
| 5,459,021 | 10/1995 | Ito et al. | 430/527 |
| 5,460,622 | 10/1995 | Dragoo et al. | 604/378 |
| 5,460,912 | 10/1995 | Yamamoto et al. | 430/93 |
| 5,460,936 | 10/1995 | Kondo et al. | 430/567 |
| 5,462,773 | 10/1995 | Swift et al. | 427/555 |
| 5,462,833 | 10/1995 | Hauquier et al. | 430/159 |
| 5,463,045 | 10/1995 | Janssens et al. | 346/158 |
| 5,463,048 | 10/1995 | Skotnicki et al. | 540/456 |
| 5,463,128 | 10/1995 | Matsushima et al. | 564/452 |
| 5,463,161 | 10/1995 | Gajda et al. | 585/671 |
| 5,463,182 | 10/1995 | Manring et al. | 525/330.4 |
| 5,463,410 | 10/1995 | Uchiyama et al. | 347/133 |
| 5,463,453 | 10/1995 | Kurotori et al. | 355/256 |
| 5,463,456 | 10/1995 | Yashiki et al. | 355/299 |

*Primary Examiner*—Angela D. Sykes
*Assistant Examiner*—Stephen Huang
*Attorney, Agent, or Firm*—Foley & Lardner

[57] ABSTRACT

A printed electrode for biological use comprises a support having thereon a printed ink paste or binder containing (a) a microgranule of at least one hydrophilic substance selected from the group consisting of hydrophilic polymers and water-soluble substances and (b) a microgranule of an electroconductive substance.

10 Claims, 3 Drawing Sheets

PRINTED ELECTRODE FOR BIOLOGICAL USE

BACKGROUND OF THE INVENTION

1. Field of the Invention

The present invention relates to a printed electrode for biological use such as a bioelectrode, typically, for example, an electrode for iontophoresis, an electrode for a low frequency current therapeutic device, or an electrode for extracting bioelectric information.

2. Description of the Related Art

In known printed electrodes for biological use, the effective area of use of the electrode interface had been the rate-determining step in the output or input of the current. For example, when use was made of silver(Ag) as the anode printed electrode for iontophoresis and silver chloride-(AgCl) was used as the cathode printed electrode, Ag is converted to AgCl on the anode surface when a current flows and, as a result, AgCl having a large electrical resistance covers the surface of Ag, the effective surface of Ag was reduced. Thus, a current value falls along with time when a constant voltage of the direct current or pulse type is applied, i.e., a so-called deterioration phenomenon of electrode appears. Further, in the case of electrodes for monitoring biological activity, this becomes a cause for occurrence of noise.

SUMMARY OF THE INVENTION

In view of the above-mentioned conditions of the prior art, the object of the present invention is to provide a printed electrode for biological use that suppresses the deterioration of the electrode by enlarging the number of electroconductive microgranules to the maximum extent, which electrode can be used on the surface of the bioelectrode and which ensures the maintenance of a stable current over a long period of time.

Other objects and advantages of the present invention will be apparent from the following description.

In accordance with the present invention, there is provided a printed electrode for biological use comprising a support having thereon a printed ink paste or binder containing (a) at least one type of hydrophilic microgranule selected from the group consisting of hydrophilic polymers and water-soluble substances and (b) an electroconductive microgranule.

BRIEF DESCRIPTION OF THE DRAWINGS

The present invention will be better understood from the description set forth below with reference to the accompanying drawings, wherein.

DESCRIPTION OF THE PREFERRED EMBODIMENT

Figure 1:
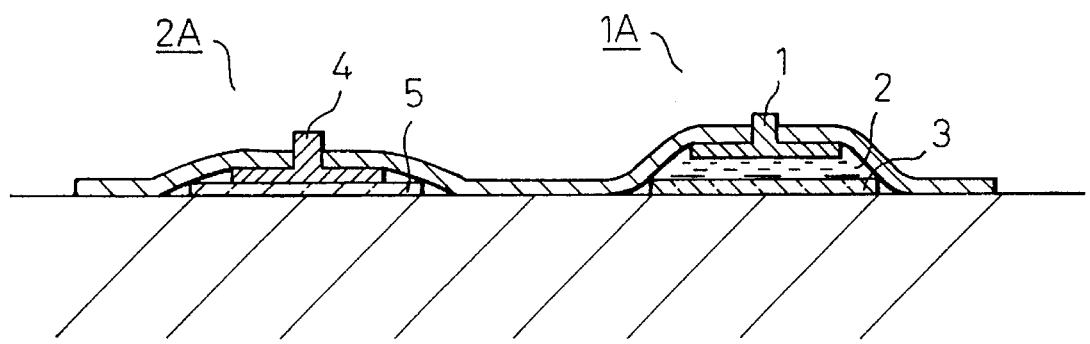
FIG. 1 is an explanatory view of illustrating an example of conventional use of iontophoresis electrode.

According to the present invention, there is provided a printed electrode for biological use obtained by impregnating, under mixing, in an ink paste and/or binder in an organic solvent having a relatively low boiling point, one or more microgranules of a hydrophilic substance such as a hydrophilic polymer, a water soluble saccharide, or a salt, together with one or more microgranules of electroconductive substance such as silver, nickel, titanium, silver chloride, or carbon, followed by printing this or directly sintering it on a support or heating it under reduced pressure or ordinary pressure to remove the organic solvent to thereby form a film or rod, whereby the effective area of the electrode surface is increased at the time of application of an aqueous solution or water-containing gel and the current stability is increased.

The features of the present invention will now be explained.

According to the electrode structure of the printed electrode for biological use of the present invention, the hydrophilic microgranules are formulated into an electroconductive ink paste. Examples of such hydrophilic substances are saccharides such as glucose, fructose, mannitol, hydrolyzed starch, D-sorbitol, xanthane gum, etc.; cellulose derivatives such as carboxymethyl-cellulose, hydroxyethylcellulose, hydroxypropyl-cellulose, carboxymethylethylcellulose etc.; hydrophilic polymers such as polyvinylalcohols, etc.; salts such as sodium chloride, potassium chloride, calcium chloride, potassium phosphate, sodium dihydrogenphosphate, potassium dihydrogenphosphate, calcium dihydrogenphosphate, sodium hydrogenphosphate, potassium hydrogenphosphate, calcium hydrogenphosphate, sodium hydrogencarbonate, sodium acetate, calcium pantothenate, and sodium pantothenate, etc.; and water soluble vitamins such as iron pyrophosphate, ascorbic acid, etc. Further, the range of the size of the granules of the hydrophiic microgranules is preferably 3 to 200 μm, more preferably 3 to 50 μm but is not particularly limited.

Further, the electrode structure of the printed electrode according to the present invention is particularly characterized by including 1 to 50% by weight, preferably 5 to 30% by weight, of the above-mentioned hydrophilic microgranules in the electroconductive metal paste ink composition comprising, as an electroconductive ink paste, at least one binder selected from the group consisting of polyesters, polypropylene, polyethylene, polyethers, polyurethanes, methacrylic resins, epoxy resins, poly(vinyl chloride), poly(vinyl acetate), poly(vinylidene chloride) and copolymers of vinyl chloride with vinyl acetate or vinylidene chloride or acrylonitrile or ethylene, and copolymers of vinyl acetate with vinylidene chloride or acrylonitrile or ethylene, in which is included 20 to 90% by weight, preferably 60 to 80% by weight, of at least one electroconductive microgranules with the range of 0.1–100 μm, selected from the group consisting of silver, silver chloride, titanium, nickel, platinum, etc.

Figure 2A:
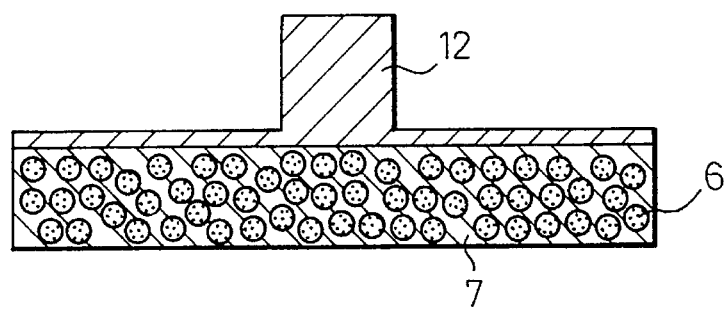
FIG. 2(a) is an explanatory view of an iontophoresis porous electrode of the present invention.
Figure 2B:
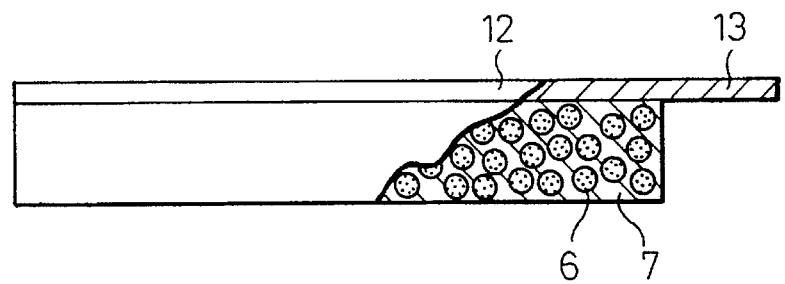
FIG. 2(b) is an explanatory view of another support for the electrode of FIG. 2(a)

We will now explain one example of the printed electrode for biological use when used as a silver chloride electrode for iontophoresis. In general, as shown in FIG. 1, the silver electrode (1) of the anode portion (1A) faces the biological surface through a drug solution holder (2) or hydrophilic gel (3), while the silver chloride electrode (4) of the cathode portion (2A) contacts the biological surface through the hydrophilic gel (5). The present invention, as shown by the example shown in FIG. 2(a), is an electrode having the structure of water soluble microgranules (6) uniformly dispersed in a silver print ink (7). When the iontophoresis is started to use, the microgranules are gradually dissolved in the water permeated from the gel or the aqueous solution. As a result, electrically, a porous electrode structure is formed. Accordingly, it becomes possible to ensure a stable current over a longer period of time, compared with a conventional silver or silver chloride printed electrode, wherein only the surface can be used. FIG. 2(b) shows a modification of the shape of the electrode support (12) comprised of the same member or a combination of different members playing the role of the support shown in FIG. 2(a) and a connection means for electrical connection with the outside. (13) is the connection terminal for electrical contact with the outside.

Further, the electrode structure of the present invention is able to sufficiently meet its objectives of use after being stored in a dry state until just before use or being stored in a moist state in contact with a gel, etc.

We will now explain an example of the method for manufacturing the electrode according to the present invention.

That is, one or more hydrophilic microgranules made of, for example, a hydrophilic polymer, water-soluble saccharide, or salt are mixed in and impregnated, together with one or more types of electroconductive microgranules (e.q., silver, nickel, titanium, silver chloride, carbon, etc.), with an ink paste or binder in an organic solvent having a relatively low boiling point printed or directly sintered on a support or heated under reduced pressure or ordinary pressure to remove the organic solvent to form a film shaped or rod shaped electrode.

Examples of the above-mentioned support are resins such as polyester, polyethylene, polypropylene, polyvinyl chloride, cellophane, nylon, polyimide, polyvinylidene chloride, polystyrene and polycarbonate, etc., nonwoven fabrics, such as cellulose, cellulose ester, nitrocellulose, rayon, polyester and nylon etc. and is formed as a member having softness or hardness, but the material and shape are not particularly limited.

Figure 3:
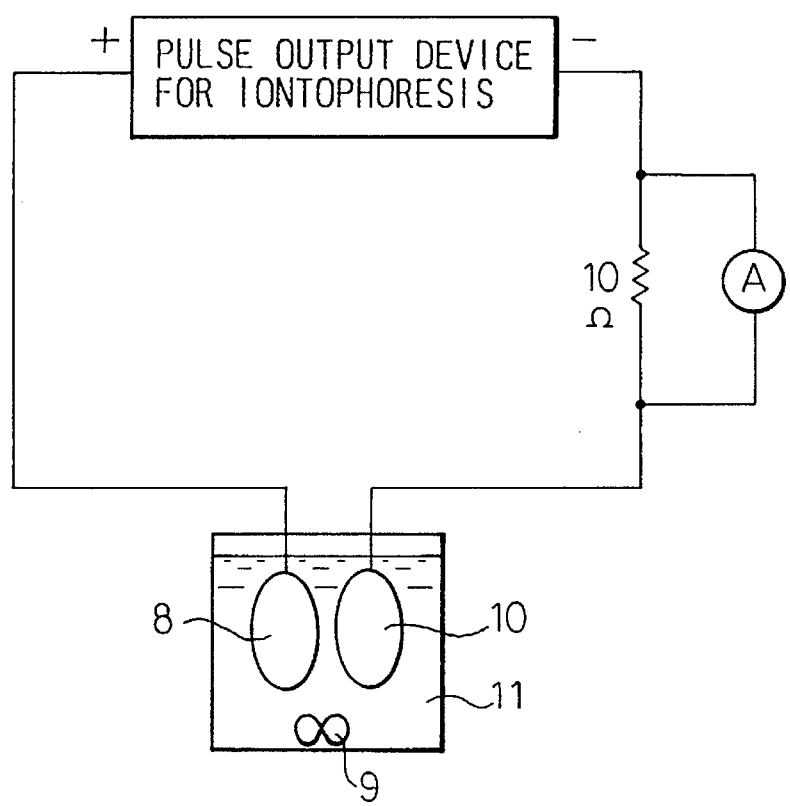
FIG. 3 is an explanatory view of a simplified experimental device of the present invention.

To further clarify the effects of the present invention, an explanation will be made of an experiment in a physiological saline solution using as an example a silver chloride electrode. The experiment was carried out using the simplified device shown in FIG. 3. The electrodes, silver and silver chloride, were set in parallel and a constant voltage of 3V was applied across the electrodes as the iontophoresis voltage. The stability of the current at that time was measured and evaluated.

EXAMPLES

The present invention will now be further illustrated by, but is by no means limited to, the following Examples.

EXAMPLE 1

Figure 4:
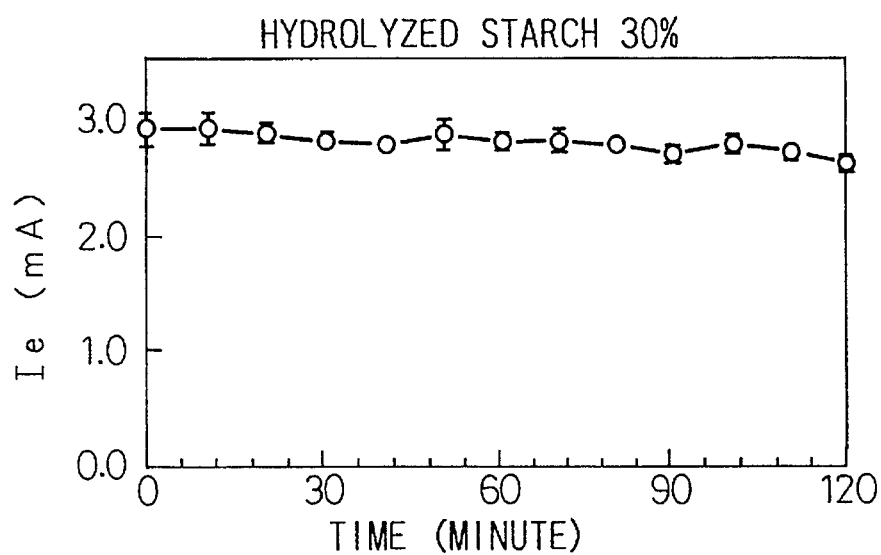
FIG. 4 is a graph illustrating the changes in the current value showing the first embodiment of the present invention.

The experiment was performed using a silver-sodium chloride electrode obtained by heating and curing a mixed ink paste comprised of 55 to 95% by weight (preferably 70% by weight) of a heat curing electroconductive silver paste "DW-250H-5" (made by Toyobo) and 5 to 45% by weight (preferably 30% by weight) of hydrolyzed starch (made by Wako Pure Chemical Industries) (where average particle size is not more than 32 μm) at 150° C. for 15 minutes. Across the anode Ag-starch and the cathode AgCl depolarizing pulsatized iontophoresis was applied, a constant voltage of 3V, 40 kHz, 30% duty. As shown in FIG. 4, a substantially stable current could be supplied even after 3 hours.

EXAMPLE 2

Figure 5:
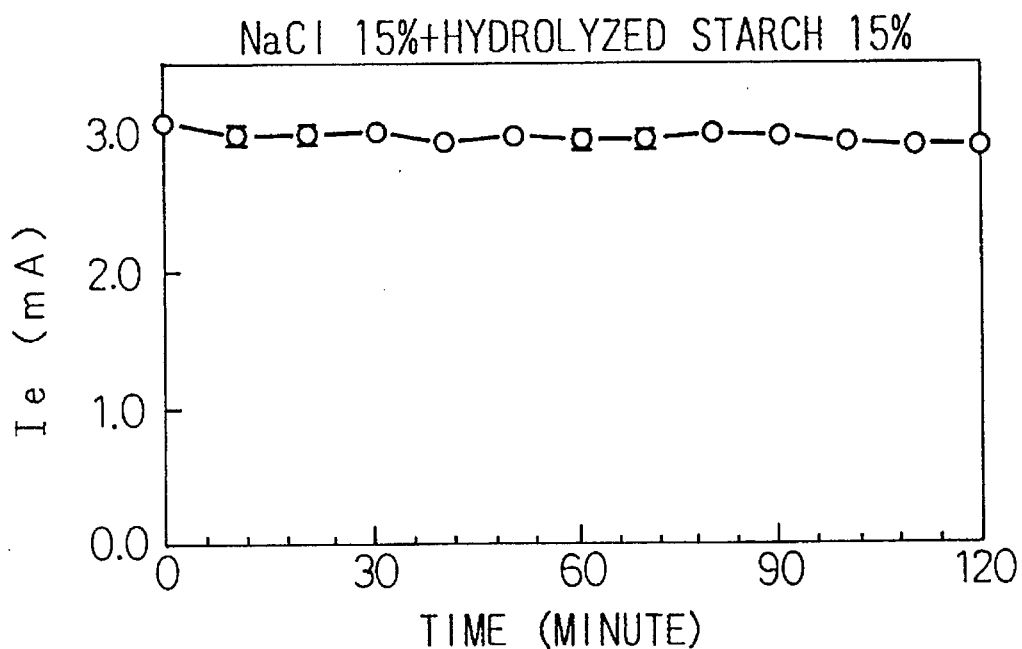
FIG. 5 is a graph illustrating the changes in the current value showing the second embodiment of the present invention.

The experiment was performed using a silver-sodium chloride-starch electrode obtained by heating and curing a mixed ink paste comprised of 55 to 95% by weight (preferably 70% by weight) of a heat curing electroconductive silver paste "DW-250H-5" (made by Toyobo), 22.5 to 2.5% by weight (preferably 15% by weight) of sodium chloride powder (where average particle size is not more than 32 μm), and 22.5 to 2.5% by weight of hydrolyzed starch (made by Wako Pure Chemical Industries) (where average particle size is not more than 32 μm) at 150° C. for 15 minutes. Across the anode Ag-starch and the cathode AgCl depolarizing pulsatized iontophoresis was applied, a constant voltage of 3V, 40 kHz, 30% duty. As shown in FIG. 5, a substantially stable current could be supplied even after 3 hours.

CONTROL EXAMPLE

Figure 6:
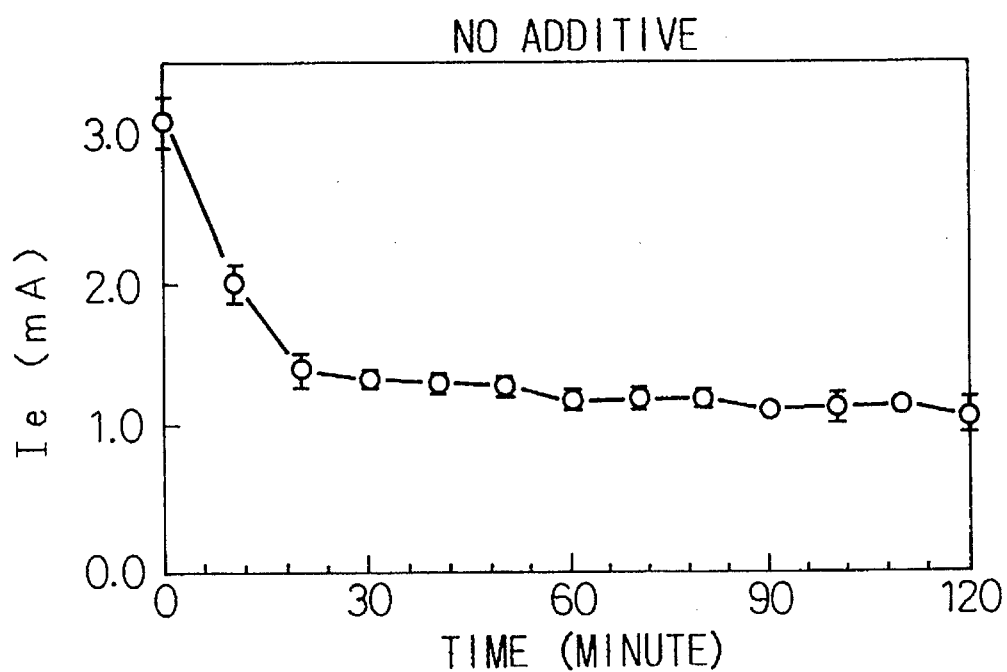
FIG. 6 is a graph illustrating the changes in the current value showing the control example of the present invention.

As a control, the experiment was conducted on just a heat cured electroconductive silver paste "DW-250H-5" (made by Toyobo), without the addition of sodium chloride, hydrolyzed starch, and other hydrophilic microgranules (additive free). The electrode curing conditions and the conduction conditions were made the same as with the above Examples. As shown in FIG. 6, compared with Example 1, in the case where no hydrophilic microgranules were added, the current value clearly fell within 15 minutes from the start of the Experiment.

As explained above, the present invention holds the water soluble microgranules or hydrophilic polymer microgranules between the electroconductive microgranules. When used as a bioelectrode, for example, when used for iontophoresis, moisture is taken up from the chlorine ion containing aqueous solution or gel by the water soluble microgranules or hydrophilic polymer microgranules and a porous electrode structure is formed during electrical conduction. As a result, it is possible to increase the effective interface surface area of the electroconductive microgranules and thereby to maintain a stable current for a long period.

Further, the present invention can be used for applications as bioelectrodes as represented by electrodes for low frequency therapeutic devices and electrodes for extracting bioelectric information in addition to the above-mentioned iontophoresis electrodes.

We claim:

1. A printed electrode for biological use comprising a support having thereon a printed ink paste or binder containing (a) a microgranule of at least one hydrophilic substance selected from the group consisting of hydrophilic polymers and water soluble substances; and (b) a microgranule of at least one electroconductive substance, wherein the microgranule of hydrophilic polymers or water soluble substances increases the dissolution thereof due to permeation of water, and wherein inclusion of water increases the microgranule of the electroconductive substance's effective surface areas.

2. A printed electrode as claimed in claim 1, wherein said hydrophilic substance is selected from the group consisting of saccharides, cellulose derivatives, salts or water-soluble vitamins.

3. A printed electrode as claimed in claim 2, wherein the hydrophilic microgranule has a particle size of 3 to 200 μm.

4. A printed electrode as claimed in claim 1, wherein said electroconductive substance is at least one member selected from the group consisting of carbon, silver, silver chloride, titanium, nickel, and platinum.

5. A printed electrode as claimed in claim 2, wherein the electroconductive microgranule has a particle size of 0.1 to 100 μm.

6. A printed electrode as claimed in claim 1, wherein said binder is at least one member selected from the group consisting of polyester polypropylene, polyethylene, polyether, polyurethane, methacrylic resin, epoxy resin, poly(vinyl chloride), poly(vinyl acetate), vinyl chloride copolymer, vinyl acetate copolymer, ethylene copolymer and vinylidene chloride copolymer.

7. A printed electrode as claimed in claim 1, wherein said electrode is contacted with a skin, at time of application, at least through water or an aqueous solution.

8. A printed electrode for biological use comprising a support having thereon a printed ink paste or binder containing (a) a microgranule of at least one hydrophilic substance selected from the group consisting of hydrophilic polymers and water soluble substances; and (b) a microgranule of at least one electroconductive substance, wherein the hydrophilic substance has a particle size of 3 to 200 μm.

9. A printed electrode for biological use comprising a support having thereon a printed ink paste or binder containing (a) a microgranule of at least one hydrophilic substance selected from the group consisting of hydrophilic polymers and water soluble substances; and (b) a microgranule of at least one electroconductive substance, wherein the electroconductive substance has a particle size of 0.1 to 100 μm.

10. A printed electrode as claimed in claim 9, wherein the hydrophilic substance has a particle size of 3 to 200 μm.

* * * * *